US006815424B2

(12) United States Patent
Vickery et al.

(10) Patent No.: US 6,815,424 B2
(45) Date of Patent: Nov. 9, 2004

(54) INTRANASAL ADMINISTRATION OF POLYPEPTIDES IN POWDERED FORM

(75) Inventors: Brian H. Vickery, Saratoga, CA (US); Eric J. Benjamin, Dublin, OH (US); Cherng-Chyi Fu, Saratoga, CA (US); Lynda M. Sanders, Palo Alto, CA (US)

(73) Assignee: Pfizer Corporation, St. Louis, MO (US)

( * ) Notice: Subject to any disclaimer, the term of this patent is extended or adjusted under 35 U.S.C. 154(b) by 0 days.

(21) Appl. No.: 10/328,409

(22) Filed: Dec. 23, 2002

(65) Prior Publication Data

US 2003/0181387 A1 Sep. 25, 2003

Related U.S. Application Data

(63) Continuation of application No. 07/902,405, filed on Jun. 19, 1992, now Pat. No. 6,521,597, which is a continuation of application No. 07/109,678, filed on Oct. 15, 1987, now abandoned.

(51) Int. Cl.$^7$ ............................................. A61K 38/00
(52) U.S. Cl. .................. 514/15; 424/400; 424/489; 424/499; 514/2; 514/12; 514/23
(58) Field of Search ............................. 514/2, 12, 15, 514/23; 424/400, 489, 499

(56) References Cited

U.S. PATENT DOCUMENTS 4,320,118 A    3/1982  White et al. ................ 424/177
4,476,116 A   10/1984  Anik ........................... 424/177
4,481,190 A   11/1984  Nestor et al. ................ 424/177
4,581,169 A    4/1986  Nestor et al. ............. 260/112.5
4,613,500 A    9/1986  Suzuki et al. ................. 429/85
4,659,693 A    4/1987  Nestor ......................... 514/12
4,690,916 A    9/1987  Nestor, Jr. et al. ............ 514/15
4,758,584 A    7/1988  Bühlmayer et al. .......... 514/400
4,801,577 A    1/1989  Nestor, Jr. et al. ............ 514/15
4,806,524 A    2/1989  Kawaguchi et al. ........... 514/8
4,824,938 A    4/1989  Koyama et al. ............. 530/351
6,521,597 B1 * 2/2003  Vickery et al. ................ 514/15

FOREIGN PATENT DOCUMENTS

EP       0 094 157 A1   11/1983   ............ A61K/9/18
EP       0 193 372       9/1986   ............ A61K/9/14

OTHER PUBLICATIONS

*Anik, S.T. et al., "Nasal Absorption of Nafarelin Acetate, the Decapeptide [D–Nal(2)6] LHRH, in Rhesus Monkeys I", J. Pharm. Sci. 73(5), 684–5 (1984).

*Nagai, T. et al., "Powder Dosage Form Of Insulin For Nasal Of Insulin For Nasal Administration", J. Control Release, 1, pp. 15–22 (1984).

* cited by examiner

Primary Examiner—Thurman K. Page
Assistant Examiner—Konata M. George
(74) Attorney, Agent, or Firm—Heller, Ehrman, White & McAuliffe, LLP

(57) ABSTRACT

Pharmaceutical compositions of biologically active polypeptides in powder form suitable for nasal administration, comprising a therapeutically effective amount of a biologically active polypeptide and a water-soluble polysaccharide.

10 Claims, No Drawings

INTRANASAL ADMINISTRATION OF POLYPEPTIDES IN POWDERED FORM

CROSS-REFERENCE TO RELATED APPLICATIONS

This application is a continuation of U.S. Ser. No. 07/902,405 filed Jun. 19, 1992, now U.S. Pat. No. 6,521,597, which is a continuation of U.S. Ser. No. 07/109,678 filed Oct. 15, 1987, now abandoned. All of which are incorporated herein by reference.

BACKGROUND OF THE INVENTION

This invention concerns pharmaceutical compositions for the intranasal administration of a biologically active polypeptide in powder form, and a method of administering such compositions. More specifically, the invention relates to pharmaceutical compositions for the intranasal administration of a therapeutically effective amount of a biologically active polypeptide, especially an LHRH analogue, in powder form suitable for intranasal administration; and to a method of administering such compositions. The intranasal compositions and methods of this invention provide effective systemic administration of therapeutically effective amounts of biologically active polypeptides, particularly in high doses.

The traditional and most widely used method of administration of therapeutic agents is by the oral route. However, in the case of polypeptides, such delivery is not feasible due to several factors, for example because of the hydrolysis of the peptides by digestive enzymes or because polypeptides are absorbed very poorly or not at all from the gastrointestinal tract. The methods most commonly used for administration of polypeptide therapeutic agents are by repeated injection, intramuscular (IM), subcutaneous (SC) or intravenous (IV) infusion. These methods are acceptable in situations where a very limited number of injections are required, or in treating life-threatening diseases, but are undesirable for chronic administration. However, the nature of many of the diseases, disorders and conditions susceptible to improvement by polypeptide administration is chronic rather than acute, thus necessitating frequent injections over a prolonged period of time. There is, therefore, a need for an efficacious and economical delivery system for polypeptide agents.

The present invention is particularly useful for the chronic administration of luteinizing hormone-releasing hormone (LHRH) analogues. The natural LHRH peptide is a decapeptide comprised of naturally occuring amino acids (which have the L-configuration except for the achiral amino acid glycine). Its sequence is as follows: (pyro)Glu-His-Trp-Ser-Tyr-Gly-Leu-Arg-Pro-Gly-NH$_2$. Many analogues of this natural material have been studied. Continuous chronic administration of LHRH agonist and antagonist analogues has been found to block the secretion of gonadotropins in both male and female animals, thereby suppressing the production of gonadal steroids and gametes. As a result, such LHRH analogues have been indicated for controlling fertility, suppressing sexual behaviour in animals, causing regression of endometriotic lesions and prostatic cancers, and in the treatment of precocious puberty and the gynecological diseases. Several methods have been proposed for the systemic delivery of LHRH analogues, but none of the methods are regarded as ideal.

As with most polypeptides, oral administration of LHRH analogues is extremely inefficient because they are inactivated or not absorbed in the gastrointestinal tract. Conventional administration of LHRH analogues includes subcutaneous and intramuscular injections. However, because LHRH analogues have short circulatory half-lives ranging from several seconds to a few hours, frequent injections are necessary to achieve effective therapeusis, rendering chronic administration difficult, inconvenient and costly.

Another approach for chronic administration of polypeptides including the LHRH analogues is the implantation or other in situ application of long acting controlled release systems. However, the implementation of such systems requires the device to be implanted and possibly to be removed surgically if interruption of treatment becomes necessary. A more broadly useful approach would be the intranasal administration of polypeptides, thus providing effective systemic administration of therapeutically effective amounts of the polypeptide without the necessity of daily or more frequent injections, or the cost and inconvenience of surgery.

The ability of certain polypeptides to be intranasally absorbed into the systemic system from nasally administered solutions in which the polypeptide is dissolved is known.

U.S. Pat. No. 4,476,116 discloses a nasal spray composition comprising an LHRH analogue and a chelating agent in an aqueous solution. The solution gave enhanced absorption compared to nasal solutions with no chelating agent.

Hirai, *Diabetes*, 27, p 296–299 (1978), discloses the nasal administration of insulin as a solution, optionally containing a surfactant, for example sodium glycholate.

However, conventional practice indicates that aqueous solutions of polypeptides provide poor bioavailability and relatively high inter-subject variability when administered nasally. Vickery et al. have disclosed intranasal administration of nafarelin acetate in aqueous solution (Transnasal Systemic Medications, ed. Y. W. Chien, Piscataway, N.J. 1985). However, the low aqueous solubility of nafarelin acetate (about 2 mg/ml in saline solution) restricts the usefulness of this approach, as in the case where a high dose of nafarelin acetate is needed to be therapeutically useful it is not possible to dissolve the required amount of nafarelin acetate in the limited amount of aqueous solution which may be introduced into the nose (about 100 $\mu$l for each nostril). Thus, in the case of nafarelin acetate, the upper dosage achievable from nasal solution is about 400 $\mu$g. As transport across the nasal membranes from such a solution is very limited, (giving about 2% bioavailability compared to injection), the total amount of nafarelin entering the bloodstream is only about 8 $\mu$g per dose.

Another disadvantage of using an aqueous solution for intranasal formulations is that polypeptides in general are less chemically stable in solution than as a solid, thus limiting the useful shelf life. Aqueous solutions also require the addition of an agent to kill microorganisms or inhibit their growth. Such agents may cause damage to nasal mucosa.

Powdered forms of polypeptides have also been intranasally administered. However, these compositions have typically required the presence of a quarternary ammonium salt, starches, sugars, water-absorbing gum, polymer, cellulose derivative or a cyclodextrin. All of these excipients have a disadvantage with regard to nasal administration. The quarternary ammonium salt and the low molecular weight water-soluble saccharides and polysaccharides generate an osmotic pressure which impedes absorption of the polypeptide by pulling water out of the nasal membranes in the opposite direction of the intended absorption. Cellulose derivatives and water absorbing/water insoluble excipients swell in the nasal membrane and present an additional layer of resistance to absorption. They also pull water out of the nasal membrane. Cyclodextrins decrease absorption by complexing with hydrophobic groups in the polypeptide. Cyclodextrins are not accepted in the World Pharmacopoeias.

European Patent Application 193,372 discloses a powdery composition for intranasal administration of polypeptides, such as calcitonin and insulin. Required in the composition is a quarternary ammonium salt and a lower alkyl ether of cellulose.

European Patent Application 122,036 discloses a formulation for powdered peptides, including LHRH, suitable for nasal administration. The formulation includes, as a required ingredient, a water-absorbing/water-insoluble base such as a starch, protein, gum or a cross-linked polymer such as polyvinylpyrrolidone, optionally in the presence of an excipient such as mannitol, sorbitol, aminoacetic acid, sodium chloride, phospholipids, etc.

Nagai, *J. Controlled Release*, 1, p 15–22 (1984) discloses a powder formulation of insulin, optionally with an excipient, for example lactose, cellulose, hydroxypropyl cellulose or carbopol 934, for nasal administration.

European Patent Application 094,157 discloses a composition comprising a highly hydrophilic drug, such as a polypeptide, polysaccharide, aminoglycoside, beta lactam antibiotic, nucleic acid, etc, in combination with a cyclodextrin, preferably α-cyclodextrin, for nasal, vaginal or rectal administration. Cyclodextrins are composed of cyclicly-linked D-glucopyranose units, α-cyclodextrin having six such units with a molecular weight of 972. Cyclodextrins are naturally occurring clathrates, i.e. they have hydrophobic cavities that form inclusion compounds with organic compounds. The cost of cyclodextrins, especially α-cyclodextrin, is generally regarded as a deterrent to widespread use of such compounds. The nasal compositions in EP 094,157 may be solid, liquid or semi-solid, optionally in combination with an excipient such as a sugar, cellulose or a cellulose derivative, polyvinylpyrrolidone, etc.

U.S. Pat. Nos. 4,010,125 and 4,476,116 disclose the preparation of certain decapeptides and claim the compounds as LHRH antagonists. Several different modes of administration of such compounds are suggested, including nasal administration. Stated to be preferred for the nasal route is an aqueous solution of the LHRH analogue. Also mentioned, but not characterized in any way, is the possibility of nasal or vaginal powders or insufflations, employing a solid carrier such as a finely-divided polyethylene glycol or lactose, optionally including other excipients such as preservatives, buffers, surface-active agents.

Thus, from an examination of the preceeding publications it may be seen that there is a need for a nasal composition capable of delivering a therapeutically useful amount of a polypeptide to an animal, such composition being a stable, non-aqueous powder free of preservatives.

SUMMARY OF THE INVENTION

Accordingly, it is an object of this invention to provide a stable pharmaceutical composition as a powder, free of preservative agents, and suitable for nasal administration of a biologically active polypeptide. The composition is capable of introducing a therapeutically useful amount of the biologically active polypeptide into the system of an animal.

A critical element in the efficacy of a nasal composition for systemic drug delivery is the rate at which the drug is transported from the composition across the nasal membranes to the systemic circulation. It is normally expected that a solution of a drug will provide faster absorption through the nasal mucosa than the same drug in a powder form, because a solution can provide better dispersion over a greater surface area, and the drug is already in the required state for transport across nasal membranes into the system. However, for the reasons delineated above, an aqueous formulation is not ideal for the nasal administration of polypeptides.

Surprisingly, it has now been found that nasal administration in powder form of a biologically active polypeptide in admixture with a high molecular weight water-soluble polysaccharide overcomes the disadvantages of nasal administration of an aqueous solution or powder formulations discussed above. In addition, it has surprisingly been found that the extent of intranasal absorption of a biologically active polypeptide from the powder composition of our invention is considerably superior to that obtained from the same dose in an aqueous solution (i.e. it provides better bioavailability). Thus a lower amount of the polypeptide is needed in each case to introduce an effective therapeutic level of the polypeptide into the systemic circulation as compared to an aqueous solution. More importantly, much higher systemic levels of a polypeptide can be achieved with the intranasal powder formulation of our invention than are possible with an aqueous formulation. Chemical stability, and consequently shelf life, is greatly extended in the solid state, and no microbiological preservatives are necessary. High molecular weight polysaccharides do not have the disadvantages of generating an osmotic pressure or forming an additional layer of resistance in nasal mucosa, as do other excipients discussed above.

As there are no solubility limitations, higher plasma concentration of an administered polypeptide may be easily achieved by merely increasing the proportion of the polypeptide in the powder formulation. This is important in the treatment of conditions that requires a high plasma concentration of a polypeptide, for example prostatic cancer and particularly precocious puberty. For such conditions it is not possible with an LHRH analogue to achieve the therapeutic levels necessary for treatment by using conventional intranasal solution formulations due to solubility limitations.

In addition to enabling the above advantages of superior absorption and higher systemic levels of intranasally administered polypeptides, the high molecular weight water-soluble polysaccharide of our invention performs the further function of providing an admixture such that a therapeutic dose of the polypeptide powder has sufficient mass for accurate weighing and delivery. This is important where the delivery is required of low doses of a highly potent polypeptide, the nasal application of which as an undiluted powder would require the manipulation of minute quantities of material.

It has also been found that the inter-subject variation in bioavailability is much reduced with the powder formulation of our invention, as compared to an aqueous solution formulation. This is a clearly advantageous virtue of the powder formulation, as the wide variation found in the bioavailability of a drug from intranasal application of an aqueous formulation gives rise to a high degree of unpredictability as to the actual therapeutic dose reaching the systemic circulation of any given subject.

In one aspect, the invention is a pharmaceutical composition for the systemic administration of a biologically active polypeptide or a pharmaceutically acceptable salt thereof to an animal in need of such a treatment, comprising a therapeutically effective amount of a biologically active polypeptide or pharmaceutically acceptable salt thereof in intimate admixture with a high molecular weight, water-soluble polysaccharide, the admixture being in a powder form suitable for nasal administration.

A preferred aspect of the invention is a pharmaceutical composition for the systemic administration of an LHRH analogue to an animal in need of such a treatment, comprising a therapeutically effective amount of an LHRH analogue or a pharmaceutically acceptable salt thereof in intimate admixture with a high molecular weight, water-soluble polysaccharide, the admixture being in powder form suitable for nasal administration.

A most preferred aspect of the invention is a pharmaceutical composition for the systemic administration of nafarelin, preferably nafarelin acetate.

Yet another aspect of this invention is a method of systemic administration of a biologically active polypeptide or a pharmaceutically acceptable salt thereof to an animal, comprising contacting with the nasal passages of an animal a therapeutically effective amount of a biologically active polypeptide or a pharmaceutically acceptable salt thereof in intimate admixture with a high molecular weight, water-soluble polysaccharide, the admixture being in powder form suitable for nasal administration.

Another preferred aspect of this invention is a method of systemic administration of an LHRH analogue to an animal comprising contacting with the nasal passages of an animal a therapeutically effective amount of an LHRH analogue or a pharmaceutically acceptable salt thereof in intimate admixture with a high molecular weight, water-soluble polysaccharide, the admixture being in powder form suitable for nasal administration.

Another most preferred aspect of this invention is a method of systemic administration of nafarelin, preferably nafarelin acetate.

DETAILED DESCRIPTION AND PREFERRED EMBODIMENTS OF THE INVENTION

As used herein, the term "a pharmaceutical composition in powder form" means a pharmaceutical composition that is in the form of a powder. The powder form consists of particles, preferably of which at least 75% are less than 100 microns in diameter, more preferably between 60 microns and 100 microns. In the practice of this invention it is preferred that substantially all particles in the powder dosage form are between 60 microns and 100 microns in diameter.

The term "nasal administration" means a systemic form of administration of an active ingredient, whereby a therapeutically effective amount of the active ingredient, for example in powdered form, is propelled or otherwise introduced into the nasal passages of an animal such that it contacts the nasal mucosa, from which it is absorbed into the systemic circulation.

The term "water-soluble polysaccharide" refers to any high-molecular weight polysaccharide (i.e. with a molecular weight of over 2000) that is soluble in water and is pharmaceutically acceptable for nasal application. Examples include dextrans and the like. A particularly preferred water-soluble polysaccharide is dextran T70.

The term "dextran" refers to polysaccharides that are composed exclusively of α-D-glucopyranosyl units, differing only in the degree of branching and chain length. Such materials are commercially available and are typically labelled to show their average molecular weight. For example, "dextran T40" refers to a mixture of such polysaccharides with an average molecular weight of 40,000, and "dextran T70" refers to a mixture of such polysaccharides with an average molecular weight of 70,000. Dextran T70 may be purchased inter alia from Pharmacia Fine Chemicals.

The term "pharmaceutically acceptable salt" refers to a salt that retains the desired biological activity of the parent compound and does not impart any undesired toxicological effects. Examples of such salts are acid addition salts formed with inorganic acids, for example hydrochloric acid, hydrobromic acid, sulfuric acid, phosphoric acid, nitric acid and the like; and salts formed with organic acids such as, for example, acetic acid, tartaric acid, succinic acid, maleic acid, fumaric acid, gluconic acid, citric acid, malic acid, ascorbic acid, benzoic acid, tannic acid, palmoic acid, alginic acid, naphthalenesulfonic acids, naphthalenedisulfonic acids and the like.

The term "intimate admixture" is intended to indicate that the biologically active polypeptide and the high molecular weight, water-soluble polysaccharide are intimately admixed such that the two components are substantially uniformly distributed within each other. Notwithstanding the use of the term "intimate", the mixture will not necessarily be entirely homogeneous throughout, but may show some variation in the relative concentrations of the two essential components of the mixture.

The term "therapeutically effective" as used herein refers to a rate and means of drug administration of a polypeptide which provides polypeptide plasma levels which are effective to achieve the desired pharmacological result. For example, if the plasma level required to achieve and maintain testosterone suppression in human males with a particular LHRH analogue is approximately 10 ng/ml, a therapeutically effective dose would be one which provides average plasma levels of that drug at or above 10 ng/ml.

The term "animal" as used herein refers to all animals in which polypeptides display useful pharmacologic effects. These include, but are not limited to, humans, horses, cattle, pigs and non-human primates and the like. The systems of this invention have particular utility in humans, in pets such as dogs and cats, in animal husbandry species such as cattle, pigs and horses, and in captive zoo animals such as lions, tigers, primates and the like.

The term "biologically active polypeptide" refers to any polypeptide having useful pharmacologic activity when administered to an animal. The composition of this invention is particularly advantageous for delivery of larger polypeptides, particularly those having molecular weights from about 1000 daltons or a pharmaceutically acceptable salt thereof, for example LHRH analogues. The preferred LHRH analogues have molecular weights in the range of about 1000 to about 1300 daltons.

Exemplary classes of polypeptides include, among others, proteins, enzymes, nucleoproteins, glycoproteins, lipoproteins, hormonally active polypeptides, and synthetic analogues including agonists and antagonists of these molecules.

The protein classes which are suitable for use in this invention are numerous, including immune modulators, lymphokines, monokines, cytokines, enzymes, antibodies, growth promotants, growth inhibitory factors, blood proteins, hormones, vaccines (including viral, bacterial, parasitic, and rickettsial antigens), blood coagulation factors and the like, including various precursor protein forms, muteins, and other analogues.

Specific examples of polypeptides suitable for incorporation in the delivery system of this invention include the following biologically active macromolecules, and muteins and other analogues thereof: interferons (α-, β-, γ- and muteins thereof, such as $\beta_{ser17}$), colony stimulating factors (1, 2, 3, GM, α-, β-, γ-, and the like), interleukins (IL-1, IL-$1_\alpha$, IL-$1_\beta$, IL-2, IL-3, IL-4, IL-5, and the like), macrophage activating factors, macrophage peptides, B cell factors (B cell growth factor and the like), T cell factors, protein A, suppressive factor of allergy, suppressor factors, cytotoxic glycoprotein, immunocytotoxic agents, immunotoxins, immunotherapeutic polypeptides, lymphotoxins, tumor necrosis factors (α-, β-, and the like), cachectin, oncostatins, tumor inhibitory factors, transforming growth factors such as TGF-α and TGF-β), albumin, alpha-1-antitrypsin, apolipoprotein-ε, erythroid potentiating factors, erythropoietin, factor VII, factor VIII(c), factor IX, fibrinolytic agent, hemopoietin-1, kidney plasminogen activator, tissue plasminogen activator, urokinase, pro-urokinase, streptokinase, lipocortin, lipomodulin, macrocortin, lung surfactant protein, protein C, protein 5, C-reactive protein, renin inhibitors, collagenase inhibitors, superoxide dismutase, epidermal growth factor, growth hormone, platelet derived growth factor, osteogenic growth factors, atrial naturetic factor, auriculin, atriopeptin, bone morphogenic protein, calcitonin, calcitonin precursor, calcitonin gene-related peptide, cartilage inducing factor, connective tissue activator protein, fertility hormones (follicle stimulating hormone, luteinizing hormone, human chorionic gonadotropin), growth hormone releasing factor, osteogenic protein, insulin, proinsulin, nerve growth factor, parathyroid hormone and analogues, parathyroid hormone antagonists, relaxin, secretin, somatomedin C, insulin-like growth factors, somatostatin and somatostatin analogues, inhibin, adrenocoricotrophic hormone, glucagon, vasoactive intestinal polypeptide, gastric inhibitory peptide, motilin, cholecystokinin, pancreatic polypeptide, gastrin releasing peptide, corticotropin releasing factor, thyroid stimulating hormone, vaccine antigens including antigens of HTLV-I, II, HTLV-III/LAV/HIV (AIDS virus), cytomegalovirus, hepatitis A, B, and non-A/non-B, herpes simplex virus-I, herpes simplex virus II, malaria, pseudorabies, retroviruses, feline leukemia virus, bovine leukemia virus, transmissible gastroenteritis virus, infectious bovine rhinotracheitis, parainfluenza, influenza, rotaviruses, respiratory syncytial virus, varicella zoster virus, Epstein-Barr virus, pertussis, and anti-infective antibodies including monoclonal and polyclonal antibodies to gram negative bacteria, pseudomonas, endotoxin, tetanus toxin, and other bacterial or viral or other infectious organisms. The lists of macromolecular polypeptides recited above are provided only to illustrate the types of active agents which are suitable for use in practicing the invention, and are not intended to be exclusive.

Classes of polypeptides which are preferred in the practice of this invention include LHRH agonists and antagonists, growth hormone releasing hormone and its analogues and antagonists, atrial natriuretic peptide (or factor), renin antagonists, parathyroid hormone and parathyroid hormone antagonists, somatostatin and somatostatin analogues, and corticotrophin releasing factor and corticotrophin releasing factor antagonists. Especially preferred growth hormone releasing hormone analogues are disclosed in U.S. Pat. No. 4,320,118 and preferred enhancers of immunological competence, (e.g. for use in treating autoimmune diseases), are disclosed in U.S. Pat. No. 4,659,693.

Growth hormone releasing hormone (GHRH) is useful in the treatment of dwarfism due to hypothalamic insufficiency, and also for treating congenital short stature. A combination of GHRH and LHRH agonists or antagonists is particularly useful in the treatment of these syndromes, as a delay or interruption of puberty, the completion of which stops further increase in height due to closure of the epiphyses of the long bones, allows for maximum benefit from the GHRH. GHRH may also be useful as a growth promoter in domestic species such as cattle or pigs.

GHRH antagonists, and somatostatin and its analogues, are useful for their insulin-sparing effects, giving better control of blood glucose in diabetics, particularly for those with Type II or non-insulin dependent diabetes. Given at night they are useful for the control of or the prevention of the "dawn phenomenon", a hyperglycemic crisis afflicting diabetics. In addition they are useful in preventing the progression of the vasculopathies (atherosclerosis, retinopathy, renopathy) and neuropathies which are complications of diabetes.

Atrial natriuretic peptide or factor (ANP or ANF) is useful in the treatment of congestive heart disease, and also the reduction of blood pressure and aldosterone in renin-dependent renovascular hypertension. Renin antagonists are also useful in the treatment of the latter condition.

Parathyroid hormone (PTH) is useful at low doses, particularly in combination with 1,25-dihydroxy vitamin $D_3$, to stop or reverse osteoporotic changes in bone, ostereoporosis caused by renal disease or corticoid therapy, senile osteoporosis and the osteoporotic changes associated with prolonged inactivity or bed rest. Calcitonin may also be useful in the treatment of osteoporosis as well as therapy for Paget's Disease. PTH antagonists may be useful in the treatment of osteoporosis as well as hyperparathyroidism and the hypercalcemia associated with malignancy.

Somatostatin (a tetradecapeptide) and its agonist analogues have the ability to suppress the secretion of a very wide range of both exocrine and endocrine secretions, and also to affect gastrointestinal motility and uptake of nutrients (see Moreau and DeFeudis, Life Sciences, Vol. 40, pp. 419–437, 1987). Their utilities stem from these inhibitory activities (as reviewed by Lamberts, Acta Endocrinologica, Suppl. Vol. 276, pp. 41–55, 1986). Examples include treatment of accromegally, insulin sparing effects, treatment of long term complications of diabetes and treatment of various endocrine secreting tumors.

Corticotrophin releasing factor (CRF) is useful in the treatment of adrenal insufficiency of hypothalamic origin. CRF antagonists may be useful for treating Addison's Disease and Cushing's Syndrome, as well as for amelioration of stress and its consequences, for example shipping fever (Bovine respiratory syndrome) or ulcers, and for alleviation of stress-induced immunosuppression.

A particularly preferred class of polypeptides are the LHRH agonists and antagonists. For convenience in describing and naming the various nona- and decapeptides within the class of LHRH agonist and antagonist analogues, the conventional abbreviations for individual amino acids are used which are recommended by the IUPAC-IUB Commission on Biochemical Nomenclature, Biochemistry, 11, 1726 (1972) and as generally accepted in the peptide art. As used herein, the abbreviations represent L-amino acids unless otherwise noted, and all peptide sequences are written according to the generally accepted convention whereby the N-terminal acid is shown on the left, and the C-terminal acid is shown on the right. Thus, "nafarelin" is a non-proprietary USAN for L-pyroglutamyl-L-histidyl-L-tryptophyl-L-seryl-L-tyrosyl-D-3-(2-naphthyl)alanyl-L-leucyl-L-arginyl-L-prolyl-glycinamide.

Certain other abbreviations are used describing many of the LHRH analogues which are advantageously incorporated in the invention. These LHRH analogues contain replacements of amino acids in the natural LHRH peptide by amino acids which do not occur in nature. Particularly commonly employed among these are the following:

| Amino acid residue | Abbreviation |
|---|---|
| 3-(2-naphthyl)-alanyl | Nal(2) |
| 3-(p-fluorophenyl)-alanyl | pF-Phe |
| 3-(p-chlorophenyl)-alanyl | pCl-Phe |
| 3-(3-pyridyl)-alanyl | Pal(3) |
| N,N'-guanidino-(dimethyl)-homoarginyl | Dmh, or hArg(Me)$_2$ |
| N,N'-guanidino-(diethyl)-homoarginyl | Deh, or hArg(Et)$_2$ |
| N,N'-guanidino-(dipropyl)-homoarginyl | Dph, or hArg(Pr)$_2$ |
| N,N'-guanidino-(diisopropyl)-homoarginyl | Dih, or hArg(iPr)$_2$ |
| N,N'-guanidino-(dihexyl)-homoarginyl | Dhh, or hArg(hexyl)$_2$ |
| N,N'-guanidino-(ethano)-homoarginyl | Eha or hArg(CH$_2$)$_2$ |
| N,N'-guanidino-(propano)-homoarginyl | Pha, or hArg(CH$_2$)$_3$ |
| N,N'-guanidino-bis-(2,2,2-trifluoroethyl)-homoarginyl | Bth, or hArg(CH$_2$CF$_3$)$_2$ |
| N-guanidino-(ethyl)-homoarginyl | Meh, or hArg(Et) |
| N-guanidino-(propyl)-homoarginyl | Prh, or hArg(propyl) |
| N-guanidino-(isopropyl)-homoarginyl | Iph, or hArg(iPr) |
| N-guanidino-(butyl)-homoarginyl | Mbh, or hArg(Bu) |
| N,N'-guanidino-(dicyclohexyl)-homoarginyl | Dch, or hArg (cyclohexyl)$_2$ |
| N-guanidino-(heptyl)-homoarginyl | Hha, or hArg(heptyl) |
| N-guanidino-(ethyl)-arginyl | Mea, or Arg(Et) |
| N,N'-guanidino-(diisopropyl)-arginyl | Dia, or Arg(iPr)$_2$ |
| N,N'-guanidino-(dicyclohexyl)-arginyl | Dca, or Arg(cyclohexyl)$_2$ |
| 3-(3-piperidyl)-alanyl | 3-Pia |
| 3-(4-piperidyl)-alanyl | 4-Pia |
| 3-((N$^\varepsilon$methyl)piperid-4-yl)-alanyl | Mpa |
| 3-((N$^\varepsilon$pentyl)piperid-4-yl)-alanyl | Ppa |
| 3-((N$^\varepsilon$-benzyl)piperid-4-yl)-alanyl | Bpa |
| N$^\varepsilon$-Nicotinyl-D-lysyl | Lys(Nic) |
| N$^\varepsilon$-(3-Pyridyl)acetyl-D-lysyl | Lys(pyridylacetyl) |
| 3-(2,4,6-trimethylphenyl)alanyl | Tmp |
| 2,2-diphenylglycyl | Dpg |

LHRH analogues comprise a large group of structurally related nona- and decapeptide analogues of naturally occurring LHRH. They are all water-soluble, polar molecules having molecular weights of about 1000–1300. The naturally occurring LHRH peptide (pyro)Glu-His-Trp-Ser-Tyr-Gly-Leu-Arg-Pro-Gly-NH$_2$ is produced in the hypothalamic region of the brain and controls the reproductive cycle of animals by acting on the anterior pituitary gland to effect release of luteinizing hormone (LH) and follicle stimulating hormone (FSH) which in turn act on the gonads to stimulate the synthesis of steroid hormones and to stimulate gamete maturation. The pulsatile release of LHRH thereby controls the reproductive cycle in animals. Additionally, LHRH has effects in the placenta, in releasing chorionic gonadotropin, directly on the gonads in rats, and on breast cancer cells.

Thus, the pharmaceutical composition of this invention may be used for a wide variety of different therapeutic applications in humans and other animals. With the particularly preferred polypeptide class, the LHRH analogues, particularly nafarelin acetate, these include, but are not limited to contraception, fertility control, suppression or interruption of heat, treatment of ovarian cysts, precocious puberty, prostatic hyperplasia and tumors, gynecologic diseases, and termination of pregnancy. The knowledge of specific utilities of LHRH analogues in various species is rapidly growing; one purpose of this invention is to provide a practical means of delivering an LHRH analogue, without being limited to any particular therapeutic application. However, specific utilities for which the invention may be particularly advantageous include the control of fertility in dogs, cats, cattle, horses, zoo animals and the like. For a summary of other potential therapeutic utilities of LHRH analogues, see Endocrine Reviews, Vol. 7, No. 1, 115–124 (1986).

Agonist analogues of LHRH are useful for the control of fertility by two mechanisms of action. Low doses of LHRH analogues can stimulate ovulation and are useful in the treatment of hypothalamic and ovulatory infertility. Additionally they can be used for hypogonadal conditions and impotence, and to stimulate spermatogenesis and androgen production in the male.

Paradoxically, larger doses of highly potent and long-lasting agonist analogues of LHRH (and LHRH itself) have an opposite effect, blocking ovulation in the female and suppressing spermatogenesis in the male. Related to these effects is a suppression of normal circulating levels of sexual steroids of gonadal origin, causing reduction in accessory organ weight in the male and female. In domestic animals this paradoxical effect promotes weight gain in a feed-lot situation, stimulates abortion in pregnant animals and in general, acts as a chemical sterilant. LHRH agonists, particularly nafarelin, methods of preparing LHRH agonists, and methods of use of such LHRH agonists are disclosed in U.S. Pat. No. 4,234,571, which is hereby incorporated in full herein by reference. A full (but not exhaustive) list of the paradoxical high dose effects of LHRH agonists is set out therein.

The most significant modification of the natural LHRH molecule with respect to LHRH agonists is obtained by changing the 6-position residue from Gly to a D-amino acid, for example, D-Ala, D-Leu, D-Phe or D-Trp. Antagonist activity can be best realized by substituting the naturally occurring 2-position His amino acid residue with with a D-amino acid residue. These analogues show increased activity relative to LHRH.

In addition to modifications at position 6, increased agonist activity may be obtained by the following modifications: modifying position 10 to afford a nonapeptide as an alkyl-, cycloalkyl- or fluoroalkyl-amine, or by replacing Gly-NH$_2$ by an α-azaglycine amide; substituting N-methyl-leucine for leucine in position 7; replacing tryptophan in position 3 by 3-(1-naphthyl)-L-alanine; substituting the position 5 tyrosine residue with phenylalanine or 3-(1-pentafluorophenyl)-L-alanine; and the substitution at position 6 of unnatural D-amino acid residues containing two or more carbocyclic (or perhydroaryl) rings or a phenyl (or cyclohexyl) ring which is highly alkyl substituted.

The LHRH agonist compounds of particular interest herein are from the last mentioned group wherein the 6-position of the naturally occurring LHRH material is replaced with a specific non-natural D-amino residue containing lipophilic carbocyclic residues, particularly residues containing two or more highly alkyl substituted carbocyclic aryl (or perhydroaryl) rings or a phenyl (or cyclohexyl) ring. These particular polypeptides are the subject of U.S. Pat. No. 4,234,571 and are prepared in accordance with the procedures set forth therein. That patent is incorporated in full herein by reference and made a part of this application. Reference is made to that application for a full description of the synthetic nonapeptides and decapeptides of most interest herein. A full description of the formulas, nomenclature and synthetic methods for preparing these compounds are found therein. The compounds set out in U.S. Pat. No. 4,234,571 are preferred synthetic LHRH analogues for incorporation into the delivery systems of this invention.

More specifically LHRH polypeptide agonists of particular interest in this invention include nonapeptides and decapeptides of the formula:

(pyro)Glu-His-V-Ser-W-X-Y-Arg-Pro-Z                 (1)

and the pharmaceutically acceptable salts thereof wherein:
V is tryptophyl, phenylalanyl or 3-(1-naphthyl)-L-alanyl;
W is tyrosyl, phenyalanyl or 3-(pentatafluoro-phenyl)-L-alanyl;
X is a D-amino acid residue

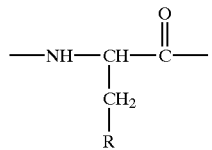

wherein R is
(a) a carbocyclic aryl-containing radical selected from the group consisting of naphthyl, anthryl, fluorenyl, phenanthryl, biphenyl, benzhydryl and phenyl substituted with three or more straight chain lower alkyl groups; or
(b) a saturated carbocyclic radical selected from the group consisting of cyclohexyl substituted with three or more straight chain lower alkyl groups, perhydro-naphthyl, perhydrobiphenylyl, perhydro-2,2-diphenylmethyl and adamantyl;
Y is leucyl, isoleucyl, nor-leucyl or N-methylleucyl;
Z is glycinamide or —NH—$R_1$, wherein $R_1$ is lower alkyl, cycloalkyl, fluoro lower alkyl or

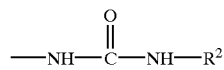

$R_2$ is hydrogen or lower alkyl.

The most preferred LHRH-active synthetic nona- and decapeptides agonists of this invention are those compounds of formula 1 wherein X is 3-(2-naphthyl)-D-alanyl or 3-(2, 4,6-trimethylphenyl)-D-alanyl-D-Deh; Z is azaglycine amide or glycinamide; V is tryptophyl or phenylalanyl; W is tyrosyl and Y is leucyl or N-methyl-leucyl.

The synthesis of LHRH analogues in general is disclosed in *Endocrine Reviews*, 7, p.44–66 (1986).

Particularly preferred LHRH agonists for use in this invention are analogues of the naturally occurring LHRH, and the pharmaceutically acceptable salts thereof, which have been modified at the 6-position residue by replacement with a natural or synthetic D-amino acid, These, listed by formula and non-proprietary USAN name, include:

| Formula of LHRH analog | Non-proprietary USAN name |
|---|---|
| 6-[3-(2-naphthalenyl)-D-alanine]LHRH; 6-[3-(2-naphthalenyl)-D-alanine]-10-azaglycinamide LHRH; | Nafarelin |
| 6-D-tryptophan LHRH; 6-D-tryptophan-7-(N-methy-L-leucine)-9-(N-ethyl-L-prolinamide)-10-desglycinamide LHRH; | Tryptorelin |
| 6-D-tryptophan-9-(N-ethyl-L-prolinamide)-10-desglycinamide LHRH; | Lutrelin |
| 6-D-leucine-9-(N-ethyl-L-prolinamide)-10-desglycinamide LHRH; | Leuprorelin (Luprolide) |
| 6-[O-(1,1-dimethylethyl)-D-serine]-9-(N-ethyl-L-prolinamide)-10-desglycinamide LHRH; | Buserelin |
| 6-[O-(1,1-dimethylethyl)-D-serine]--10-azaglycinamide LHRH; and | Goserelin |
| 6-[1-(phenylmethyl)-D-histidine]-9-(N-ethyl-L-prolinamide)-10-desglycinamide LHRH. | Histrelin |

There is also the group of LHRH analogues termed antagonists. These polypeptides antagonize the effect of endogenous LHRH at low dose levels relative to naturally occurring LHRH. Such compounds are to be included within the scope of this invention.

Particularly potent LHRH antagonists are described in U.S. Pat. Nos. 4,481,190 and 4,581,169, and in U.S. patent application Ser. No. 495,226 filed May 20, 1983, each of which is incorporated by reference herein. Preferred LHRH antagonists useful in this invention include:

[N—Ac-$\Delta^3$-Pro$^1$, D-pF-Phe$^2$, Detirelix D-Trp$^{3,6}$, NMeLeu$^7$]LHRH;
[N—Ac-$\Delta^3$-Pro$^1$, D-pF-Phe$^2$, D-Nal(2)$^{3,6}$]LHRH;
[N—Ac-Pro$^1$, D-pF-Phe$^2$, D-Nal(2)$^{3,6}$]LHRH;
[N—Ac-Ala$^1$, D-pF-Phe$^2$, D-Trp$^{3,6}$]LHRH;
[N—Ac-D-Trp$^1$, D-pCl-Phe$^2$, D-Trp$^3$, D-Phe$^6$, D-Ala$^{10}$]LHRH;
[N—Ac-D-Trp$^1$, D-pCl-Phe$^2$, D-Trp$^3$, D-Arg$^6$, D-Ala$^{10}$]LHRH;
[N—Ac-D-pCl-Phe$^1$, D-pCl-Phe$^2$, D-Trp$^3$, D-Arg$^6$, D-Ala$^{10}$]LHRH;
[N—Ac-D-Nal(2)$^1$, D-pF-Phe$^2$, D-Trp$^3$, D-Arg$^6$]LHRH;
[N—Ac-D-Nal(2)$^1$, D-pF-Phe$^2$, D-Trp$^3$, oCl-Phe$^5$, D-Arg$^6$]LHRH;
[N—Ac-D-pBr-Phe$^1$, D-pCl-Phe$^2$, D-Trp$^3$, D-Arg$^6$, D-Ala$^{10}$]LHRH;
[N—Ac-D-Nal(2)$^1$, D-pCl-Phe$^2$, D-Trp$^3$, D-Arg$^6$, D-Ala$^{10}$]LHRH;
[N—Ac-D-Nal(2)$^1$, D-pCl-Phe$^2$, D-Pal(3)$^3$, D-Arg$^6$, D-Ala$^{10}$]LHRH;
[N—Ac-D-Nal(2)$^1$, D-pCl-Phe$^2$, D-Pal(3)$^3$, D-Arg$^6$, D-Trp$^7$, D-Ala-$^{10}$]LHRH;
[N—Ac-D-Nal(2)$^1$, D-pCl-Phe$^2$, D-Pal(3)$^3$, D-Arg$^6$, D-Ile$^7$, D-Ala$^{10}$]LHRH;
[N—Ac-D-Nal(2)$^1$, D-αMe,pCl-Phe$^2$, D-Trp$^3$, Arg$^5$, D-Tyr$^6$, D-Ala$^{10}$]LHRH;
[N—Ac-D-Nal(2)$^1$, D-αMe,pCl-Phe$^2$, D-Pal(3)$^3$, D-Arg$^6$, N-iPrLys$^8$, D-Ala$^{10}$]LHRH;
[N—Ac-D-Nal(2)$^1$, D-pCl-Phe$^2$, D-Trp$^3$, D-Deh$^6$, D-Ala$^{10}$]LHRH;
[N—Ac-D-Nal(2)$^1$, D-pF-Phe$^2$, D-Trp$^3$, D-Deh$^6$, D-Ala$^{10}$]LHRH;
[N—Ac-D-Nal(2)$^1$, D-pCl-Phe$^2$, D-Trp$^3$, D-F-Deh$^6$, D-Ala$^{10}$]LHRH; and
[N—Ac-D-Nal(2)$^1$, D-pCl-Phe$^2$, D-Trp$^3$, D-Deh$^6$, Aza-Gly$^{10}$]LHRH.

Further preferred LHRH antagonists are those disclosed in U.S. patent application Ser. No. 07/010,923, now U.S. Pat. No. 4,801,577 issued Jan. 31, 1989, filed Feb. 5, 1987, the entirety of which is incorporated herein by reference. Of these, the following are particularly preferred LHRH antagonists for incorporation in the formulation of this invention.

N—Ac-D-Nal(2)-D-pCl-Phe-D-Pal(3)-Ser-Tyr-D-Pal(3)-Leu-Deh-Pro-D-AlaNH$_2$;

N—Ac-D-Nal(2)-D-pCl-Phe-D-Pal(3)-Ser-Tyr-D-Pal(3)-Leu-Bth-Pro-D-AlaNH$_2$;

N—Ac-D-Nal(2)-D-pCl-Phe-D-Pal(3)-Ser-Tyr-D-Pal(3)-Leu-Mbh-Pro-D-AlaNH$_2$;

N—Ac-D-Nal(2)-D-pCl-Phe-D-Pal(3)-Ser-Tyr-D-Pal(3)-Leu-Pha-Pro-D-AlaNH$_2$;

N—Ac-D-Nal(2)-D-pCl-Phe-D-Trp-Ser-Tyr-D-Trp-Leu-Deh-Pro-D-AlaNH$_2$;

N—Ac-D-Nal(2)-D-pCl-Phe-D-Trp-Ser-Tyr-D-Trp-Leu-Bth-Pro-D-AlaNH$_2$;

N—Ac-D-Nal(2)-D-pCl-Phe-D-Trp-Ser-Tyr-D-Trp-Leu-Mbh-Pro-D-AlaNH$_2$;

N—Ac-D-Nal(2)-D-pCl-Phe-D-Trp-Ser-Tyr-D-Trp-Leu-Pha-Pro-D-AlaNH$_2$;

N—Ac-D-Nal(2)-D-pCl-Phe-D-Trp-Ser-Tyr-D-Deh-Leu-Deh-Pro-D-AlaNH$_2$;

N—Ac-D-Nal(2)-D-pCl-Phe-D-Trp-Ser-Tyr-D-Mbh-Leu-Mbh-Pro-D-AlaNH$_2$;

N—Ac-D-Nal(2)-D-pCl-Phe-D-Trp-Ser-Tyr-D-Bth-Leu-Bth-Pro-D-AlaNH$_2$;

N—Ac-D-Nal(2)-D-pCl-Phe-D-Trp-Ser-Tyr-D-Pha-Leu-Pha-Pro-D-AlaNH$_2$;

N—Ac-D-Nal(2)-D-pCl-Phe-D-Pal(3)-Ser-Tyr-D-Deh-Leu-Deh-Pro-D-AlaNH$_2$;

N—Ac-D-Nal(2)-D-pCl-Phe-D-Pal(3)-Ser-Tyr-D-Mbh-Leu-Mbh-Pro-D-AlaNH$_2$;

N—Ac-D-Nal(2)-D-pCl-Phe-D-Pal(3)-Ser-Tyr-D-Bth-Leu-Bth-Pro-D-AlaNH$_2$;

N—Ac-D-Nal(2)-D-pCl-Phe-D-Pal(3)-Ser-Tyr-D-Pha-Leu-Pha-Pro-D-AlaNH$_2$;

N—Ac-D-Nal(2)-D-pCl-Phe-D-Trp-Ser-Arg-D-Trp-Leu-Deh-Pro-D-AlaNH$_2$;

N—Ac-D-Nal(2)-D-pCl-Phe-D-Trp-Ser-Arg-D-Trp-Leu-Bth-Pro-D-AlaNH$_2$;

N—Ac-D-Nal(2)-D-pCl-Phe-D-Trp-Ser-Arg-D-Trp-Leu-Mbh-Pro-D-AlaNH$_2$;

N—Ac-D-Nal(2)-D-pCl-Phe-D-Trp-Ser-Arg-D-Trp-Leu-Pha-Pro-D-AlaNH$_2$;

N—Ac-D-Nal(2)-D-pCl-Phe-D-Pal(3)-Ser-Arg-D-Pal(3)-Leu-Bth-Pro-D-AlaNH$_2$;

N—Ac-D-Nal(2)-D-pCl-Phe-D-Pal(3)-Ser-Arg-D-Pal(3)-Leu-Mbh-Pro-D-AlaNH$_2$;

N—Ac-D-Nal(2)-D-pCl-Phe-D-Pal(3)-Ser-Arg-D-Pal(3)-Leu-Deh-Pro-D-AlaNH$_2$;

N—Ac-D-Nal(2)-D-pCl-Phe-D-Pal(3)-Ser-Arg-D-Pal(3)-Leu-Pha-Pro-D-AlaNH$_2$;

N—Ac-D-Nal(2)-D-pCl-Phe-D-Trp-Ser-Arg-D-Tyr-Leu-Deh-Pro-D-AlaNH$_2$;

N—Ac-D-Nal(2)-D-pCl-Phe-D-Trp-Ser-Arg-D-Tyr-Leu-Bth-Pro-D-AlaNH$_2$;

N—Ac-D-Nal(2)-D-pCl-Phe-D-Trp-Ser-Arg-D-Tyr-Leu-Mbh-Pro-D-AlaNH$_2$;

N—Ac-D-Nal(2)-D-pCl-Phe-D-Trp-Ser-Arg-D-Tyr-Leu-Pha-Pro-D-AlaNH$_2$;

N—Ac-D-Nal(2)-D-pCl-Phe-D-Pal(3)-Ser-Arg-D-Tyr-Leu-Bth-Pro-D-AlaNH$_2$;

N—Ac-D-Nal(2)-D-pCl-Phe-D-Pal(3)-Ser-Arg-D-Tyr-Leu-Mbh-Pro-D-AlaNH$_2$;

N—Ac-D-Nal(2)-D-pCl-Phe-D-Pal(3)-Ser-Arg-D-Tyr-Leu-Deh-Pro-D-AlaNH$_2$;

N—Ac-D-Nal(2)-D-pCl-Phe-D-Pal(3)-Ser-Arg-D-Tyr-Leu-Pha-Pro-D-AlaNH$_2$;

N—Ac-D-Nal(2)-D-pCl-Phe-D-Trp-Ser-Deh-D-Tyr-Leu-Deh-Pro-D-AlaNH$_2$;

N—Ac-D-Nal(2)-D-pCl-Phe-D-Trp-Ser-Mbh-D-Tyr-Leu-Mbh-Pro-D-AlaNH$_2$;

N—Ac-D-Nal(2)-D-pCl-Phe-D-Trp-Ser-Bth-D-Tyr-Leu-Bth-Pro-D-AlaNH$_2$;

N—Ac-D-Nal(2)-D-pCl-Phe-D-Trp-Ser-Pha-D-Tyr-Leu-Pha-Pro-D-AlaNH$_2$;

N—Ac-D-Nal(2)-D-pCl-Phe-D-Trp-Ser-Deh-D-Trp-Leu-Deh-Pro-D-AlaNH$_2$;

N—Ac-D-Nal(2)-D-pCl-Phe-D-Trp-Ser-Mbh-D-Trp-Leu-Mbh-Pro-D-AlaNH$_2$;

N—Ac-D-Nal(2)-D-pCl-Phe-D-Trp-Ser-Bth-D-Trp-Leu-Bth-Pro-D-AlaNH$_2$;

N—Ac-D-Nal(2)-D-pCl-Phe-D-Trp-Ser-Pha-D-Trp-Leu-Pha-Pro-D-AlaNH$_2$;

N—Ac-D-Nal(2)-D-pCl-Phe-D-Pal(3)-Ser-Deh-D-Pal(3)-Leu-Deh-Pro-D-AlaNH$_2$;

N—Ac-D-Nal(2)-D-pCl-Phe-D-Pal(3)-Ser-Mbh-D-Pal(3)-Leu-Mbh-Pro-D-AlaNH$_2$;

N—Ac-D-Nal(2)-D-pCl-Phe-D-Pal(3)-Ser-Bth-D-Pal(3)-Leu-Bth-Pro-D-AlaNH$_2$;

N—Ac-D-Nal(2)-D-pCl-Phe-D-Pal(3)-Ser-Pha-D-Pal(3)-Leu-Pha-Pro-D-AlaNH$_2$;

N—Ac-D-Nal(2)-D-pCl-Phe-D-Trp-Ser-Deh-D-Nal(2)-Leu-Deh-Pro-D-AlaNH$_2$;

N—Ac-D-Nal(2)-D-pCl-Phe-D-Trp-Ser-Mbh-D-Nal(2)-Leu-Mbh-Pro-D-AlaNH$_2$;

N—Ac-D-Nal(2)-D-pCl-Phe-D-Trp-Ser-Bth-D-Nal(2)-Leu-Bth-Pro-D-AlaNH$_2$;

N—Ac-D-Nal(2)-D-pCl-Phe-D-Trp-Ser-Pha-D-Nal(2)-Leu-Pha-Pro-D-AlaNH$_2$;

N—Ac-D-Nal(2)-D-pCl-Phe-D-Pal(3)-Ser-Pal(3)-D-Pal(3)-Leu-Deh-Pro-D-AlaNH$_2$;

N—Ac-D-Nal(2)-D-pCl-Phe-D-Pal(3)-Ser-Pal(3)-D-Pal(3)-Leu-Bth-Pro-D-AlaNH$_2$;

N—Ac-D-Nal(2)-D-pCl-Phe-D-Pal(3)-Ser-Pal(3)-D-Pal(3)-Leu-Pha-Pro-D-AlaNH$_2$;

N—Ac-D-Nal(2)-D-pCl-Phe-D-Pal(3)-Ser-Pal(3)-D-Pal(3)-Leu-Mbh-Pro-D-AlaNH$_2$;

N—Ac-D-Nal(2)-D-pCl-Phe-D-Pal(3)-Ser-Tyr-D-Mbh-Leu-Bth-Pro-D-AlaNH$_2$;

N—Ac-D-Nal(2)-D-pCl-Phe-D-Trp-Ser-Tyr-D-Mbh-Leu-Bth-Pro-D-AlaNH$_2$;

N—Ac-D-Nal(2)-D-pF-Phe-D-Pal(3)-Ser-Tyr-D-Pal(3)-Leu-Deh-Pro-D-AlaNH$_2$;

N—Ac-D-Nal(2)-D-pF-Phe-D-Pal(3)-Ser-Tyr-D-Pal(3)-Leu-Bth-Pro-D-AlaNH$_2$;

N—Ac-D-Nal(2)-D-pF-Phe-D-Trp-Ser-Tyr-D-Trp-Leu-Deh-Pro-D-AlaNH$_2$;

N—Ac-D-Nal(2)-D-pF-Phe-D-Trp-Ser-Tyr-D-Trp-Leu-Bth-Pro-D-AlaNH$_2$;

N—Ac-D-Nal(2)-D-pF-Phe-D-Trp-Ser-Tyr-D-Deh-Leu-Deh-Pro-D-AlaNH$_2$;

N—Ac-D-Nal(2)-D-pF-Phe-D-Trp-Ser-Tyr-D-Bth-Leu-Bth-Pro-D-AlaNH$_2$;

N—Ac-D-Nal(2)-D-pF-Phe-D-Pal(3)-Ser-Tyr-D-Deh-Leu-Deh-Pro-D-AlaNH$_2$;

N—Ac-D-Nal(2)-D-pF-Phe-D-Pal(3)-Ser-Tyr-D-Bth-Leu-Bth-Pro-D-AlaNH$_2$;

N—Ac-D-Nal(2)-D-pF-Phe-D-Trp-Ser-Arg-D-Trp-Leu-Deh-Pro-D-AlaNH$_2$;

N—Ac-D-Nal(2)-D-pF-Phe-D-Trp-Ser-Arg-D-Trp-Leu-Bth-Pro-D-AlaNH$_2$;

N—Ac-D-Nal(2)-D-pF-Phe-D-Pal(3)-Ser-Arg-D-Pal(3)-Leu-Bth-Pro-D-AlaNH$_2$;
N—Ac-D-Nal(2)-D-pF-Phe-D-Pal(3)-Ser-Arg-D-Pal(3)-Leu-Deh-Pro-D-AlaNH$_2$;
N—Ac-D-Nal(2)-D-pF-Phe-D-Trp-Ser-Deh-D-Tyr-Leu-Deh-Pro-D-AlaNH$_2$; and
N—Ac-D-Nal(2)-D-pF-Phe-D-Trp-Ser-Bth-D-Tyr-Leu-Bth-Pro-D-AlaNH$_2$.

The scope of the instant invention also includes LHRH analogues that may not necessarily fall within the aforementioned preferred classes, such as:
N—Ac-D-Nal(2)-D-pCl-Phe-D-Trp-Ser-Tyr-D-Tyr-Leu-Deh-Pro-D-AlaNH$_2$;
N—Ac-D-Nal(2)-D-pCl-Phe-D-Trp-Ser-Tyr-D-Tyr-Leu-Mbh-Pro-D-AlaNH$_2$;
N—Ac-D-Nal(2)-D-pCl-Phe-D-Trp-Ser-Tyr-D-Tyr-Leu-Bth-Pro-D-AlaNH$_2$;
N—Ac-D-Nal(2)-D-pCl-Phe-D-Trp-Ser-Tyr-D-Tyr-Leu-Pha-Pro-D-AlaNH$_2$;
N—Ac-D-Nal(2)-D-pCl-Phe-D-Pal(3)-Ser-Tyr-D-Nal(2)-Leu-Deh-Pro-D-AlaNH$_2$;
N—Ac-D-Nal(2)-D-pCl-Phe-D-Pal(3)-Ser-Tyr-D-Nal(2)-Leu-Mbh-Pro-D-AlaNH$_2$;
N—Ac-D-Nal(2)-D-pCl-Phe-D-Pal(3)-Ser-Tyr-D-Nal(2)-Leu-Bth-Pro-D-AlaNH$_2$;
N—Ac-D-Nal(2)-D-pCl-Phe-D-Pal(3)-Ser-Tyr-D-Nal(2)-Leu-Pha-Pro-D-AlaNH$_2$;
N—Ac-D-Nal(2)-D-αMe,pCl-Phe-D-Pal(3)-Ser-Arg-D-Pal(3)-Leu-Bth-Pro-D-AlaNH$_2$;
N—Ac-D-Nal(2)-D-αMe,pCl-Phe-D-Pal(3)-Ser-Tyr-D-Pal(3)-Leu-Bth-Pro-D-AlaNH$_2$;
N—Ac-D-Nal(2)-b-αMe,pCl-Phe-D-Trp-Ser-Arg-D-Trp-Leu-Bth-Pro-D-AlaNH$_2$;
N—Ac-D-Nal(2)-D-pCl-Phe-D-Pal(3)-Ser-Tyr-D-Glu(AA)-Leu-Bth-Pro-D-AlaNH$_2$;
N—Ac-D-Nal(2)-D-pCl-Phe-D-Pal(3)-Ser-Arg-D-Glu(AA)-Leu-Bth-Pro-D-AlaNH$_2$;
N—Ac-D-Nal(2)-D-pCl-Phe-D-Trp-Ser-Arg-D-Glu(AA)-Leu-Bth-Pro-D-AlaNH$_2$;
N—Ac-D-pCl-Phe-D-Phe-D-Phe-Ser-Phe-D-Lys(Nic)-Nle-Bth-Pro-GlyNH$_2$;
N—Ac-$\Delta^{3,4}$Pro-D-Nal(2)-D-Pal(3)-Ser-Pal(3)-D-Lys(pyridylacetyl)-Phe-Mpa-D-AlaNH$_2$;
N—Ac-Pro-D-pNO$_2$-Phe-D-Trp-Ser-Phe-D-Lys(Nic)-Leu-Ppa-Pro-D-LeuNH$_2$;
N—Ac-D-pF-Phe-D-pF-Phe-D-Trp-Ser-Tyr-D-Tyr-Trp-Bth-Pro-AzaGlyNH$_2$;
N—Ac-D-Nal(1)-Dpg-D-Pal(3)-Ser-Tyr-D-Pal(3)-Nal(2)-Bth-Pro-D-AlaNH$_2$;and
N—Ac-D-Tmp-D-pF-Phe-D-Pal(3)-Ser-Tyr-D-Lys(Nic)-Nal(2)-Bth-Pro-NHEt.

These specific compounds represent some of the more useful fertility affecting LHRH type polypeptides which have been developed to date. This is not intended to be an exhaustive or exclusive list of all LHRH active polypeptides which have been made or which can or may be made. They are simply set out to illustrate the type of compounds which are the subject of this invention. Any or all of them can be interchangeably substituted into the compositions of this invention. The preferred LHRH agonist of the present invention is nafarelin and salts of nafarelin, particularly nafarelin acetate. The preferred LHRH antagonists of the present invention are: [N—Ac-D-Nal(2)$^1$, D-pCl-Phe$^2$, D-Trp$^3$, D-Deh$^6$, D-Ala$^{10}$]LHRH, N—Ac-D-Nal(2)-D-pCl-Phe-D-Pal(3)-Ser-Tyr-D-Deh-Leu-Deh-Pro D-AlaNH$_2$, N—Ac-D-Nal(2)-D-pCl-Phe-D-Pal(3)-Ser-Tyr-D-Pal(3)-Leu-Deh-Pro-D-AlaNH$_2$; and the pharmaceutically acceptable salts thereof.

A preferred embodiment of this invention is nafarelin acetate in powdered form in admixture with a water soluble polysaccharide excipient in powdered form. A particularly preferred polysaccharide is dextran, more particularly dextran T70.

In a most preferred embodiment, the nafarelin acetate and dextran T70 intimately admixed are in the form of a powder in which at least 75% of the particles in the powder are below 100 microns in diameter, preferably between 60 microns and 100 microns, especially where substantially all of the particles in the powder are between 60 microns and 100 microns in diameter.

The relative proportions of polypeptide and polysaccharide components within the formulation can be varied depending on the polypeptide to be administered and the dosage level desired. The polypeptide active agent may comprise up to about 40 weight percent of the formulation. The precise amount will depend on such factors as the potency of the particular active agent, its physicochemical and pharmacokinetic behaviour, its stability and the condition being treated.

A preferred composition for the formulation comprises, by weight:
(a) 60 to 99.9999 percent polysaccharide; and
(b) 0.0001 to 40 percent biologically active polypeptide.

The present invention is well-suited to the controlled delivery of LHRH analogues. The amount of LHRH analogue incorporated with the polysaccharide will preferably be 20%, or less, depending on the particular LHRH analogue and the other factors listed above. A presently preferred composition comprises, by weight:
(a) 80 to 99.999 percent polysaccharide; and
(b) 0.001 to 20 percent LHRH analogue.

A more preferred composition comprises, by weight:
(a) 80 to 99.999 percent dextran T70; and
(b) 0.001 to 20 percent LHRH analogue.

A most preferred composition comprises, by weight:
(a) 92 to 98 percent dextran T70; and
(b) 2 to 8 percent nafarelin acetate.

The powder compositions of this invention may also include an absorption enhancer. A second preferred composition for such a formulation comprises, by weight:
(a) 50 to 99.8999 percent polysaccharide;
(b) 0.0001 to 40 percent biologically active polypeptide; and
(c) 0.1 to 10 percent absorption enhancer.

A more preferred composition comprises, by weight:
(a) 75 to 98.999 percent dextran T70;
(b) 0.001 to 20 percent LHRH analog; and
(c) 1 to 5 percent bile acid surfactant.

A most preferred composition comprises, by weight:
(a) 89 to 97 percent dextran T70;
(b) 2 to 8 percent nafarelin acetate; and
(c) 1 to 3 percent sodium glycocholate.

As used herein, the term "absorption enhancer" refers to a material or compound which, when incorporated in the powder mixture, causes further enhancement of the total amount of the polypeptide absorbed intranasally into the systemic circulation from the powder formulation.

The preferred agents optionally used for enhancing the absorption of polypeptides across the nasal membrane from the powder formulations are bile acid surfactants, or a pharmaceutically acceptable salt thereof.

These acids are, for example, glycocholic acid, cholic acid, taurocholic acid, cholanic acid, ethocholic acid, desoxycholic acid, chenodesoxycholic acid, dehydrocholic acid and glycodeoxy-cholic acid. One or more acids or salts may be used, but preferably a single pharmaceutically acceptable acid salt is used in the powder formulation.

The pharmaceutically acceptable surfactant salt will be any salt which retains the phenomena of enhanced peptide absorption, as well as the compound's surfactant characteristics, and which are not deleterious to the subject or otherwise contraindicated. Such salts are for example those salts derived from inorganic bases which include sodium, potassium, ammonium, calcium, ferrous, zinc, manganous, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, tromethamine, dicyclohexylamine, choline and caffeine.

More preferably, the surfactant used in the practice of this invention will be an alkali metal salt of glycocholic acid, most preferably sodium glycocholate.

The amount of surfactant, when used in the practice of this invention, is in the range between about 0.2 and 15%. It is preferred that the surfactant be present in an amount between about 0.5 to 4 percent by weight, most preferably about 2 percent by weight.

Methods of Preparation

The powder formulations of this invention are made by conventional techniques. For a discussion of the state of the art, see, for example, *Remington's Pharmaceutical Sciences*, Mack Publishing Company, Easton, Pa., 18th Edition, 1975, particularly from page 1554 to page 1575. Preferred methods include freeze drying a solution and precipitating the powder from solution.

For example, a suitable formulation of a polypeptide in powdered form is made by first forming a solution of the polypeptide. The solution preferably also contains the high molecular weight polysaccharide, for example dextran, as required in the final formulation, and optionally the absorption enhancer, for example sodium glycocholate. The solvent is preferably largely composed of water, although the water may contain amounts of other polar solvents, for example, methanol or ethanol.

The solvent is then removed by lyophilization, or the like, or the solids are precipitated and removed by filtration or similar techniques. If the particles of the resulting solid are too large for nasal administration, the solid must be processed further. The next step in the process is pulverization. Suitable methods for pulverization include cutting, chopping, crushing, grinding, milling, micronization, screening, trituration, or the like.

The resulting particles are then size classified. Suitable size classification methods include screening, sieving and the like. Particles of the preferred size in the powder of this invention, i.e. particles that are less than 100 microns in diameter, preferably between 60 microns and 100 microns in diameter, are obtained by passing the powder through a #200 standard mesh.

The preceding discussion is not exhaustive. Alternate methods can be used to form the composition of the present invention. For example, powders of ingredients of the desired particle size can first be made independently and then subsequently mixed, thereby forming a powder form of the composition of this invention.

Utility

One aspect of the present invention is a method of nasally administering polypeptides useful for treating physiological conditions requiring the systemic administration of a polypeptide. Examples of physiological conditions or diseases that are treatable with systemically administered polypeptides, especially LHRH analogues, include malignancies, especially prostatic cancer, and breast cancer; hormonally-dependent disorders of the reproductive organs, especially endometriosis, polycystic ovarian syndrome, uterine leiomyata, pre-menstrual syndrome, and fibrocystic breast disease; benign prostatic hyperplasia; precocious puberty; delay of normal puberty; treatment of male infertility; treatment of female infertility; and female contraception. The nasally administered powder may contain more than one active ingredient. For example, an LHRH medication for prostatic cancer might include an anti-androgen to combat androgen elevation often seen at the beginning of LHRH therapy, or an LHRH medication for breast cancer might include an anti-estrogen. Two polypeptides, for example an LHRH agonist or antagonist combined with GHRH, may be used in the treatment of dwarfism or short stature. While therapeutic dose levels of the polypeptides will vary greatly depending on the potency or pharmacological properties of the particular analogue and the nature of the therapy being provided, the following statements provide an indication of the general broad ranges of dose levels that are presently understood to be useful:

Dose levels in the pharmaceutical composition of the present invention of an LHRH analogue useful in the treatment of prostatic cancer in men are generally between about 100 $\mu$g and 4 mg, preferably between about 300 $\mu$g and 2 mg.

Dose levels in the pharmaceutical composition of the present invention of an LHRH analogue useful in the treatment of endometriosis or other gynecological disorders in women are generally between about 100 $\mu$g and 1 mg.

Dose levels in the pharmaceutical composition of the present invention of an LHRH analogue useful for blocking ovulation in women are-generally between about 100 $\mu$g and 1 mg.

Dose levels in the pharmaceutical composition of the present invention of an LHRH analogue useful for treating precocious puberty are generally between about 200 $\mu$g and 4 mg.

However, ascertaining or defining the required dose level of a particular polypeptide is a routine aspect of the art and is well within the level of ordinary skill. It should be understood that the limiting amount for nasal administration of a powder is probably about 10 mg per nostril.

Method of Administration

The powder formulation, once made, is preferably propelled into the nasal passages of the subject animal. Any suitable apparatus and/or method for placing a pharmaceutical dose into the nasal passages of a subject animal that can be adapted to the delivery of a powder, can be used. Such apparatus or method preferably propels the powder into the nostril under positive pressure. For example, the powdered formulation is placed in an L shaped glass tube with a nozzle tip. The tube is connected to a source of a controlled amount of slightly compressed air, for example to a syringe with an extended plunger, by a flexible connection. The tip is placed in the nostril of the subject animal and the powder is propelled into the subject's nasal passages under positive external pressure, for example, by depressing the plunger.

The following Preparations and Examples are provided to further illustrate practical means and/or tests for carrying out the invention described and claimed herein, and should not be interpreted as limiting it in any way. From the foregoing description, one of ordinary skill can easily ascertain and adapt the essential characteristics of the invention to particular needs or situations without departing from the spirit and scope thereof.

Preparation 1

Standard Reference Solution

An amount of nafarelin acetate equivalent to 2.0 mg of nafarelin as the free base, 50 mg sorbitol, 0.1 mg benzalkonium chloride, 1.2 mg acetic acid and enough purified water to bring the volume of the solution to 1 ml are mixed together. This solution is referred to as the standard solution hereinafter.

EXAMPLE 1

Freeze Dried Powder Formulation

An amount of nafarelin acetate equivalent to 10 mg of nafarelin as the free base and 240 mg of dextran T70 were dissolved together in purified water. A powdered formulation having 4 wt. % nafarelin (weight of nafarelin as the free base) was then made by freeze drying the solution, grinding the product in a pestle and mortar and passing the resultant powder through a #200 standard mesh.

Similarly, by varying the proportion of nafarelin acetate to dextran T70 and following the procedure above, 2 wt % and 8 wt. % powdered formulations were prepared.

Similarly, by substituting other polypeptides, for example leuprorelin, somatostatin analogues or detirelix, for nafarelin acetate in the above description, other pharmaceutical compositions of our invention are made.

EXAMPLE 1A

Freeze Dried Powder Formulation Containing an Absorption Enhancer

An amount of nafarelin acetate equivalent to 10 milligrams of nafarelin as the free base, 235 mg of dextran T70 and 5 mg of sodium glycocholate were dissolved together in purified water. A powdered formulation having 4 wt. % of nafarelin (weight of nafarelin as the free base) and 2 wt. % of sodium glycocholate was then made by freeze drying the solution, grinding the product in a pestle and mortar and passing the resultant powder through a #200 standard mesh.

Similarly, by varying the proportion of nafarelin acetate to dextran T70 and following the procedure above, 2. wt % and 8 wt % powdered formulations were prepared.

Similarly, by substituting other polypeptides, for example leuprorelin, somatostatin analogues or detirelix, for nafarelin acetate in the above description and optionally substituting various quantities of other absorption enhancers for sodium glycocholate, other pharmaceutical compositions of our invention are made.

EXAMPLE 2

Method of Administration of Powder

The powdered formulation (5 mg) of Example 1 or 1A was weighed accurately and transferred quantitatively into an L shaped glass tube with a nozzle tip. The tube was connected using rubber tubing to a 5 ml syringe with the plunger pulled out. The nozzle was placed in the nostril of the subject animal and the powder propelled into the nostril by pushing the plunger all the way down in one quick motion. This was repeated with another tube containing the powder for the second nostril. The total delivery was 10 mg of powder. This device and technique gave consistent and complete delivery of the powder formulation.

Alternatively, the powder formulation can be suspended in an aerosolizing vehicle such as freon, or other fluorocarbons, and delivered into the nasal passages as a fine mist or vapor.

EXAMPLE 3

Plasma Levels of Nafarelin in Rhesus Monkeys Following Intranasal Administration of Solution and Powder Formulations TABLE 1 compares the peak blood levels of nafarelin in rhesus monkeys after they were given doses of nafarelin in standard solution form, prepared as shown in Preparation 1, and powder forms containing different percentages of active ingredient, prepared as shown in Example 1 (i.e. without an absorption enhancer). The powder forms were applied using the technique described in Example 2, and the solution was applied as a divided dose administered to each nostril, suitably by means of a spray. Suitably a spray bottle with a metered dose (conveniently 100 µl per spray) pump attachment was used.

The serum levels of nafarelin in the subject rhesus monkeys were measured by radio-immunoassay for nafarelin. The technique is described in *Analytical Biochemistry*, 141, p10–16, (1984). All the serum levels of nafarelin were measured in the same way.

As can be seen from the table, the powder formulation gives higher peak blood levels of nafarelin (about three times more) than the standard solution formulation containing an identical amount of nafarelin acetate.

The dose level of 800 µg is not achievable by the solution formulation, since only 100 µl of solution can be administered to each nostril, and nafarelin acetate is insufficiently soluble to give more than a maximum of about 200 µg in 100 µl of solution.

The theoretical values shown in TABLE 1 are calculated based on the assumption that if the dose and concentration of nafarelin is doubled, the peak blood levels should be doubled. Thus it can be seen that the actually observed values show an unexpected result: as the dose of nafarelin is doubled the blood level of nafarelin increases at a much greater rate than doubling.

TABLE 1

Peak Blood Levels in Rhesus Monkeys

| Formulation | Dosage (µg) | No. in Group | Peak Blood Levels (ng/ml) |
|---|---|---|---|
| Observed | | | |
| 2% powder | 200 | 3 | 6 ± 4 |
| 4% powder | 400 | 3 | 22 ± 8 |
| 8% powder | 800 | 3 | 76 ± 8 |

TABLE 1-continued

Peak Blood Levels in Rhesus Monkeys

| Formulation | Dosage (µg) | No. in Group | Peak Blood Levels (ng/ml) |
|---|---|---|---|
| Theoretical | | | |
| 2% powder | 200 | | 6 |
| 4% powder | 400 | | 12 |
| 8% powder | 800 | | 24 |
| Solution | | | |
| Standard Solution | 400 | 6 | 8 ± 7 |

TABLE 2 shows the Area Under the Curve (AUC) for blood levels achieved from various doses of nafarelin in a powdered formulation and a solution formulation. Again much more nafarelin absorption than theoretically expected is seen in the blood levels in the higher doses.

AUC is the area under the plasma concentration-time curve. This area is directly proportional to the total amount of unchanged drug that has entered the systemic circulation, and is an important measure of bioavailability.

TABLE 2

Area Under the Curve (AUC)

| Formulation Strength | No. in Group | Dose (µg) | AUC 8 hours ng/Hr/ml |
|---|---|---|---|
| Observed | | | |
| 2% powder | 3 | 200 | 10 ± 3 |
| 4% powder | 3 | 400 | 39 ± 4 |
| 8% powder | 3 | 800 | 127 ± 9 |
| Theoretical | | | |
| 2% powder | | 200 | 10 |
| 4% powder | | 400 | 20 |
| 8% powder | | 800 | 40 |
| Standard Solution | | | |
| Standard solution | 6 | 400 | 14 ± 5 |

Table 3 shows the inter-subject variability of the peak height and the AUC for various formulations in rhesus monkeys. Lower numbers in the table for the % coefficient of variation demonstrates less variation in peak height and the AUC from subject to subject for the same dose. The table shows that the powder formulation of this invention provides a substantially smaller % coefficient of variation than the standard solution.

TABLE 3

Inter-subject variation of the absorption of nafarelin

| SPECIES | FORMULATION | DOSE µg | NUMBER IN GROUP | % COEFFICIENT OF VARIATION | |
|---|---|---|---|---|---|
| | | | | Peak Height | AUC 8 Hrs |
| Rhesus | Standard Solution | 400 | 6 | 89 | 34 |
| | 4% nafarelin + dextran T70 | 400 | 3 | 20 | 11 |
| | 8% nafarelin + Dextran T70 | 800 | 3 | 11 | 7 |

EXAMPLE 4

Comparison in Humans of the Efficacy of Single-Dose Administration of Solution and Powder Formulations of Nafarelin Acetate The table below compares the area under the curve (AUC) for nafarelin in humans after being given doses of nafarelin acetate in powder form, prepared as shown in Example 1 (i.e. without absorption enhancer), or standard solution form described as described in Preparation 1. The powder form was administered using the technique described in Example 2. The solution form was administered using the conventional technique as described in Example 3. As the table shows, the powder form gave substantially higher blood levels than the solution having the same amount of nafarelin acetate. The AUC achieved with the 800 µg powder dose is not attainable by administration of a solution, due to the low solubility of nafarelin acetate, as discussed in more detail in Example 3.

The serum levels of nafarelin were measured by radio-immunoassay for nafarelin. The technique is described in *Analytical Biochemistry*, 141, p10–16, (1984).

| Formulation | Nafarelin Dose (µg) | Number in Study | 0–8 hr AUC Value (ng/ml per hr) |
|---|---|---|---|
| Standard Solution | 400 | 6 | 3.2 |
| 4% nafarelin + dextran T70 | 400 | 6 | 4.6 |
| 8% nafarelin + Dextran T70 | 800 | 6 | 8.0 |

EXAMPLE 5

Comparison of Efficacy of Two Different Powder Formulations

The table shows the difference between the plasma levels of nafarelin for two different formulations. The same amount of each formulation was tested in a series of the same three rhesus monkeys. The powder form was administered using the technique described in Example 2. The values in the table are the average values for all three monkeys. Formulation #1 is made as described in Example 1, but with 4 wt % nafarelin acetate in polyvinylpyrrolidone in place of dextran T70. Formulation #2 was made as in Example 1 with 4 wt % nafarelin in dextran T70.

As the table below shows, the nafarelin is far more bioavailable in the dextran T70 (formulation #2) than the polyvinylpyrrolidone (formulation #1), indicating that the high molecular weight water-soluble polysaccharides of our invention are superior formulating agents for nasal dosage forms of nafarelin.

| | Plasma Concentrations of Nafarelin (ng/ml) | |
|---|---|---|
| TIME | FORMULATION #1 | FORMULATION #2 |
| 5 MIN | 0.02 | 2.24 |
| 15 MIN | 0.12 | 18.07 |
| 30 MIN | 0.29 | 22.17 |
| 1 HOUR | 0.93 | 14.7 |
| 2 HOURS | 0.54 | 6.03 |
| 4 HOURS | 0.21 | 1.74 |
| 8 HOURS | 0.06 | 0.64 |

EXAMPLE 6

Enhancement of the Absorption of Nafarelin in Rhesus Monkeys from a Powder Formulation by Incorporation of Sodium Glycocholate The powder formulations prepared as described in Examples I and IA were administered as single 100 mg doses to rhesus monkeys. Resulting peak blood levels of nafarelin are given in the following table which shows that nafarelin is more bioavailable in the enhanced powder formulation than in the standard powder formulation.

| Formulation | Dosage (μg) | No. in Group | Peak Blood Levels (ng/ml) |
|---|---|---|---|
| Observed | | | |
| 4% powder | 400 | 3 | 22 ± 8 |
| 4% powder + 2% sodium glycocholate | 400 | 3 | 76 ± 8 |

EXAMPLE 7

Comparison of the Absorption of Leuprorelin in Rhesus Monkeys When Administered as a Powder Formulation

| Formulation | Dosage | No. in Group | Peak Blood Levels (ng/ml) |
|---|---|---|---|
| Observed | | | |
| 10% Luprorelin 90% Dextran T70 | 1 mg | 3 | <40 |
| 20% Luprorelin 80% Dextran T70 | 2 mg | 3 | 89 ± 20 |

No blood levels of leuprorelin were detected in following the administration of 10% leuprorelin in Dextran T70. It is shown as less than 40 ng/ml in the table above, as 40 ng/ml of leuprorelin is the lower limit of detection of Leuprolide by the method used. For the same reason, no comparison with solution formulations of leuprorelin are possible, as the dose level of leuprorelin required to produce detectable amounts of leuprorelin in the blood (i.e. 40 ng/ml) are not attainable with solution formulations, being beyond the upper limit of solubility of leuprorelin in such formulations.

Thus it can be seen that a twofold increase of leuprorelin in the administered dose gives more than a twofold increase in leuprorelin found in the peak blood level.

EXAMPLE 8

Plasma Levels of Detirelix in Rhesus Monkeys Following Intranasal Administration of Solution and Powder Formulations

| Formulation | Dosage (μg) | No. in Group | Peak Blood Levels (ng/ml) |
|---|---|---|---|
| Observed | | | |
| Detirelix 0.17% in sorbitol, glacial acetic acid and water (solution) | 340 | 6 | 3.9 ± 0.9 |
| Detirelix 3.4% in Dextran T70 (powder) | 340 | 9 | 5.4 ± 0.6 |

The table shows that detirelix is more bioavailable as a powder formulation than as a standard aqueous solution formulation.

EXAMPLE 9

Plasma Levels of GHRH in Rhesus Monkeys Following Intranasal Administration of Solution and Powder Formulations This was an internally controlled study using the same animals (designated as (1) or (2)), thus minimizing the influence of variables such as individual differences in anatomy or disease which might otherwise affect absorption.

| Formulation | Dosage (μg) | Peak Blood Levels (ng/ml) |
|---|---|---|
| Observed | | |
| GHRH 2.0 mg/ml in 5% sorbitol, glacial acetic acid and water (solution) | 400 400 | 39.8 (1) 43.5 (2) |
| GHRH 4% in Dextran T70 (powder) | 400 400 | 81.6 (1) 93.4 (2) |

(GHRH is Growth Hormone Releasing Hormone.)

As can be seen from the above table, GHRH is absorbed more than twice as efficiently from the powder formulation as compared to the solution formulation.

What is claimed is:

1. A powdered pharmaceutical composition for the intranasal administration of an LHRH analogue selected from the group consisting of

[N—Ac-$\Delta^3$-Pro$^1$, D-pF-Phe$^2$, D-Nal(2)$^{3,6}$]LHRH,

[N—Ac-Pro$^1$, D-pF-Phe$^2$, D-Nal(2)$^{3,6}$]LHRH,

[N—Ac-Ala$^1$, D-pF-Phe$^2$, D-Trp$^{3,6}$]LHRH,

[N—Ac-D-Trp$^1$, D-pCl-Phe$^2$, D-Trp$^3$, D-Phe$^6$, D-Ala$^{10}$] LHRH,

[N—Ac-D-Trp$^1$, D-pCl-Phe$^2$, D-Trp$^3$, D-Arg$^6$, D-Ala$^{10}$] LHRH,

[N—Ac-D-pCl-Phe$^1$, D-pCl-Phe$^2$, D-Trp$^3$, D-Arg$^6$, D-Ala$^{10}$]LHRH,

[N—Ac-D-Nal(2)$^1$, D-pF-Phe$^2$, D-Trp$^3$, D-Arg$^6$]LHRH,

[N—Ac-D-Nal(2)$^1$, D-pF-Phe$^2$, D-Trp$^3$, oCl-Phe$^5$, D-Arg$^6$]LHRH,

[N—Ac-D-pBr-Phe$^1$, D-pCl-Phe$^2$, D-Trp$^3$, D-Arg$^6$, D-Ala$^{10}$]LHRH,

[N—Ac-D-Nal(2)$^1$, D-pCl-Phe$^2$, D-Trp$^3$, D-Arg$^6$, D-Ala$^{10}$]LHRH,

[N—Ac-D-Nal(2)$^1$, D-pCl-Phe$^2$, D-Pal(3)$^3$, D-Arg$^6$, D-Ala$^{10}$]LHRH,

[N—Ac-D-Nal(2)$^1$, D-pCl-Phe$^2$, D-Pal(3)$^3$, D-Arg$^6$, D-Trp$^7$, D-Ala$^{10}$]LHRH,

[N—Ac-D-Nal(2)[1], D-pCl-Phe[2], D-Pal(3)[3], D-Arg[6], D-Ile[7], D-Ala[10]]LHRH,

[N—Ac-D-Nal(2)[1], D-αMe, pCl-Phe[2], D-Trp[3], Arg[5], D-Tyr[6], D-Ala[10]]LHRH,

[N—Ac-D-Nal(2)[1], D-αMe, pCl-Phe[2], D-Pal(3)[3], D-Arg[6], N-iPrLys[8], Ala[10]]LHRH,

[N—Ac-D-Nal(2)[1], D-pF-Phe[2], D-Trp[3], D-Deh[6], D-Ala[10]]LHRH,

[N—Ac-D-Nal(2)[1], D-pCl-Phe[2], D-Trp[3], D-F-Deh[6], D-Ala[10]]LHRH,

[N—Ac-D-Nal(2)[1], D-pCl-Phe[2], D-Trp[3], D-Deh[6], Aza-Gly[10]]LHRH,

N—Ac-D-Nal(2)-D-pCl-Phe-D-Pal(3)-Ser-Tyr-D-Pal(3)-Leu-Bth-Pro-D-AlaNH$_2$,

N—Ac-D-Nal(2)-D-pCl-Phe-D-Pal(3)-Ser-Tyr-D-Pal(3)-Leu-Mbh-Pro-D-AlaNH$_2$,

N—Ac-D-Nal(2)-D-pCl-Phe-D-Pal(3)-Ser-Tyr-D-Pal(3)-Leu-Pha-Pro-D-AlaNH$_2$,

N—Ac-D-Nal(2)-D-pCl-Phe-D-Trp-Ser-Tyr-D-Trp-Leu-Deh-Pro-D-AlaNH$_2$,

N—Ac-D-Nal(2)-D-pCl-Phe-D-Trp-Ser-Tyr-D-Trp-Leu-Bth-Pro-D-AlaNH$_2$,

N—Ac-D-Nal(2)-D-pCl-Phe-D-Trp-Ser-Tyr-D-Trp-Leu-Mbh-Pro-D-AlaNH$_2$,

N—Ac-D-Nal(2)-D-pCl-Phe-D-Trp-Ser-Tyr-D-Trp-Leu-Pha-Pro-D-AlaNH$_2$,

N—Ac-D-Nal(2)-D-pCl-Phe-D-Trp-Ser-Tyr-D-Deh-Leu-Deh-Pro-D-AlaNH$_2$,

N—Ac-D-Nal(2)-D-pCl-Phe-D-Trp-Ser-Tyr-D-Mbh-Leu-Mbh-Pro-D-AlaNH$_2$,

N—Ac-D-Nal(2)-D-pCl-Phe-D-Trp-Ser-Tyr-D-Bth-Leu-Bth-Pro-D-AlaNH$_2$,

N—Ac-D-Nal(2)-D-pCl-Phe-D-Trp-Ser-Tyr-D-Pha-Leu-Pha-Pro-D-AlaNH$_2$,

N—Ac-D-Nal(2)-D-pCl-Phe-D-Pal(3)-Ser-Tyr-D-Mbh-Leu-Mbh-Pro-D-AlaNH$_2$,

N—Ac-D-Nal(2)-D-pCl-Phe-D-Pal(3)-Ser-Tyr-D-Bth-Leu-Bth-Pro-D-AlaNH$_2$,

N—Ac-D-Nal(2)-D-pCl-Phe-D-Pal(3)-Ser-Tyr-D-Pha-Leu-Pha-Pro-D-AlaNH$_2$,

N—Ac-D-Nal(2)-D-pCl-Phe-D-Trp-Ser-Arg-D-Trp-Leu-Deh-Pro-D-AlaNH$_2$,

N—Ac-D-Nal(2)-D-pCl-Phe-D-Trp-Ser-Arg-D-Trp-Leu-Bth-Pro-D-AlaNH$_2$,

N—Ac-D-Nal(2)-D-pCl-Phe-D-Trp-Ser-Arg-D-Trp-Leu-Mbh-Pro-D-AlaNH$_2$,

N—Ac-D-Nal(2)-D-pCl-Phe-D-Trp-Ser-Arg-D-Trp-Leu-Pha-Pro-D-AlaNH$_2$,

N—Ac-D-Nal(2)-D-pCl-Phe-D-Pal(3)-Ser-Arg-D-Pal(3)-Leu-Bth-Pro-D-AlaNH$_2$,

N—Ac-D-Nal(2)-D-pCl-Phe-D-Pal(3)-Ser-Arg-D-Pal(3)-Leu-Mbh-Pro-D-AlaNH$_2$,

N—Ac-D-Nal(2)-D-pCl-Phe-D-Pal(3)-Ser-Arg-D-Pal(3)-Leu-Deh-Pro-D-AlaNH$_2$,

N—Ac-D-Nal(2)-D-pCl-Phe-D-Pal(3)-Ser-Arg-D-Pal(3)-Leu-Pha-Pro-D-AlaNH$_2$,

N—Ac-D-Nal(2)-D-pCl-Phe-D-Trp-Ser-Arg-D-Tyr-Leu-Deh-Pro-D-AlaNH$_2$,

N—Ac-D-Nal(2)-D-pCl-Phe-D-Trp-Ser-Arg-D-Tyr-Leu-Bth-Pro-D-AlaNH$_2$,

N—Ac-D-Nal(2)-D-pCl-Phe-D-Trp-Ser-Arg-D-Tyr-Leu-Mbh-Pro-D-AlaNH$_2$,

N—Ac-D-Nal(2)-D-pCl-Phe-D-Trp-Ser-Arg-D-Tyr-Leu-Pha-Pro-D-AlaNH$_2$,

N—Ac-D-Nal(2)-D-pCl-Phe-D-Pal(3)-Ser-Arg-D-Tyr-Leu-Bth-Pro-D-AlaNH$_2$,

N—Ac-D-Nal(2)-D-pCl-Phe-D-Pal(3)-Ser-Arg-D-Tyr-Leu-Mbh-Pro-D-AlaNH$_2$,

N—Ac-D-Nal(2)-D-pCl-Phe-D-Pal(3)-Ser-Arg-D-Tyr-Leu-Deh-Pro-D-AlaNH$_2$,

N—Ac-D-Nal(2)-D-pCl-Phe-D-Pal(3)-Ser-Arg-D-Tyr-Leu-Pha-Pro-D-AlaNH$_2$,

N—Ac-D-Nal(2)-D-pCl-Phe-D-Trp-Ser-Deh-D-Tyr-Leu-Deh-Pro-D-AlaNH$_2$,

N—Ac-D-Nal(2)-D-pCl-Phe-D-Trp-Ser-Mbh-D-Tyr-Leu-Mbh-Pro-D-AlaNH$_2$,

N—Ac-D-Nal(2)-D-pCl-Phe-D-Trp-Ser-Bth-D-Tyr-Leu-Bth-Pro-D-AlaNH$_2$,

N—Ac-D-Nal(2)-D-pCl-Phe-D-Trp-Ser-Pha-D-Tyr-Leu-Pha-Pro-D-AlaNH$_2$,

N—Ac-D-Nal(2)-D-pCl-Phe-D-Trp-Ser-Deh-D-Trp-Leu-Deh-Pro-D-AlaNH$_2$,

N—Ac-D-Nal(2)-D-pCl-Phe-D-Trp-Ser-Mbh-D-Trp-Leu-Mbh-Pro-D-AlaNH$_2$,

N—Ac-D-Nal(2)-D-pCl-Phe-D-Trp-Ser-Bth-D-Trp-Leu-Bth-Pro-D-AlaNH$_2$,

N—Ac-D-Nal(2)-D-pCl-Phe-D-Trp-Ser-Pha-D-Trp-Leu-Pha-Pro-D-AlaNH$_2$,

N—Ac-D-Nal(2)-D-pCl-Phe-D-Pal(3)-Ser-Deh-D-Pal(3)-Leu-Deh-Pro-D-AlaNH$_2$,

N—Ac-D-Nal(2)-D-pCl-Phe-D-Pal(3)-Ser-Mbh-D-Pal(3)-Leu-Mbh-Pro-D-AlaNH$_2$,

N—Ac-D-Nal(2)-D-pCl-Phe-D-Pal(3)-Ser-Bth-D-Pal(3)-Leu-Bth-Pro-D-AlaNH$_2$,

N—Ac-D-Nal(2)-D-pCl-Phe-D-Pal(3)-Ser-Pha-D-Pal(3)-Leu-Pha-Pro-D-AlaNH$_2$,

N—Ac-D-Nal(2)-D-pCl-Phe-D-Trp-Ser-Deh-D-Nal(2)-Leu-Deh-Pro-D-AlaNH$_2$,

N—Ac-D-Nal(2)-D-pCl-Phe-D-Trp-Ser-Mbh-D-Nal(2)-Leu-Mbh-Pro-D-AlaNH$_2$,

N—Ac-D-Nal(2)-D-pCl-Phe-D-Trp-Ser-Bth-D-Nal(2)-Leu-Bth-Pro-D-AlaNH$_2$,

N—Ac-D-Nal(2)-D-pCl-Phe-D-Trp-Ser-Pha-D-Nal(2)-Leu-Pha-Pro-D-AlaNH$_2$,

N—Ac-D-Nal(2)-D-pCl-Phe-D-Pal(3)-Ser-Pal(3)-D-Pal(3)-Leu-Deh-Pro-D-AlaNH$_2$,

N—Ac-D-Nal(2)-D-pCl-Phe-D-Pal(3)-Ser-Pal(3)-D-Pal(3)-Leu-Bth-Pro-D-AlaNH$_2$,

N—Ac-D-Nal(2)-D-pCl-Phe-D-Pal(3)-Ser-Pal(3)-D-Pal(3)-Leu-Pha-Pro-D-AlaNH$_2$,

N—Ac-D-Nal(2)-D-pCl-Phe-D-Pal(3)-Ser-Pal(3)-D-Pal(3)-Leu-Mbh-Pro-D-AlaNH$_2$,

N—Ac-D-Nal(2)-D-pCl-Phe-D-Pal(3)-Ser-Tyr-D-Mbh-Leu-Bth-Pro-D-AlaNH$_2$,

N—Ac-D-Nal(2)-D-pCl-Phe-D-Trp-Ser-Tyr-D-Mbh-Leu-Bth-Pro-D-AlaNH$_2$,

N—Ac-D-Nal(2)-D-pF-Phe-D-Pal(3)-Ser-Tyr-D-Pal(3)-Leu-Deh-Pro-D-AlaNH$_2$,

N—Ac-D-Nal(2)-D-pF-Phe-D-Pal(3)-Ser-Tyr-D-Pal(3)-Leu-Bth-Pro-D-AlaNH$_2$,

N—Ac-D-Nal(2)-D-pF-Phe-D-Trp-Ser-Tyr-D-Trp-Leu-Deh-Pro-D-AlaNH$_2$,

N—Ac-D-Nal(2)-D-pF-Phe-D-Trp-Ser-Tyr-D-Trp-Leu-Bth-Pro-D-AlaNH$_2$,

N—Ac-D-Nal(2)-D-pF-Phe-D-Trp-Ser-Tyr-D-Deh-Leu-Deh-Pro-D-AlaNH$_2$,

N—Ac-D-Nal(2)-D-pF-Phe-D-Trp-Ser-Tyr-D-Bth-Leu-Bth-Pro-D-AlaNH$_2$,

N—Ac-D-Nal(2)-D-pF-Phe-D-Pal(3)-Ser-Tyr-D-Deh-Leu-Deh-Pro-D-AlaNH$_2$,

N—Ac-D-Nal(2)-D-pF-Phe-D-Pal(3)-Ser-Tyr-D-Bth-Leu-Bth-Pro-D-AlaNH$_2$,

N—Ac-D-Nal(2)-D-pF-Phe-D-Trp-Ser-Arg-D-Trp-Leu-Deh-Pro-D-AlaNH$_2$,

N—Ac-D-Nal(2)-D-pF-Phe-D-Trp-Ser-Arg-D-Trp-Leu-Bth-Pro-D-AlaNH$_2$,

N—Ac-D-Nal(2)-D-pF-Phe-D-Pal(3)-Ser-Arg-D-Pal(3)-Leu-Bth-Pro-D-AlaNH$_2$,

N—Ac-D-Nal(2)-D-pF-Phe-D-Pal(3)-Ser-Arg-D-Pal(3)-Leu-Deh-Pro-D-AlaNH$_2$,

N—Ac-D-Nal(2)-D-pF-Phe-D-Trp-Ser-Deh-D-Tyr-Leu-Deh-Pro-D-AlaNH$_2$, and

N—Ac-D-Nal(2)-D-pF-Phe-D-Trp-Ser-Bth-D-Tyr-Leu-Bth-Pro-D-AlaNH$_2$ or a pharmaceutically acceptable salt thereof to an animal in need of such a treatment, which composition comprises a therapeutically effective amount of the LHRH analogue or pharmaceutically acceptable salt thereof in intimate admixture with a high molecular weight, water-soluble polysaccharide having a molecular weight greater than about 2000 Daltons.

2. A pharmaceutical composition of claim 1 comprising from about 2 to about 8 weight percent LHRH analogue and from about 98 to about 92 weight percent water soluble polysaccharide.

3. The composition of claim 1 wherein the water-soluble polysaccharide is dextran.

4. The composition of claim 3 wherein the pharmaceutically acceptable salt is the acetate.

5. A pharmaceutical composition for the systemic administration of the LHRH analogue of claim 1 to an animal in need of such a treatment, which composition consists essentially of a therapeutically effective amount of the LHRH analogue in intimate admixture with dextran, the admixture being in a powder form, wherein a least 75% of the particles of the powder form have diameters of between about 60 microns and 100 microns.

6. The composition of claim 1 wherein the powder form includes an absorption enhancer.

7. The composition of claim 6 wherein the absorption enhancer is a bile acid surfactant.

8. The composition of claim 6 wherein the absorption enhancer is sodium glycocholate.

9. A method for the systemic administration of a biologically active polypeptide comprising contacting the nasal passages of an animal in need of treatment with a biologically effective amount of the composition of claim 1.

10. A method of systemic administration of the LHRH analogue of claim 1 to an animal, which method consists essentially of contacting with the nasal passages of the animal an intimate admixture of a therapeutically effective amount of the LHRH analogue and dextran T70, the admixture being in a powder form, wherein at least 75% of the particles of the powder form have a diameter of between 60 microns and 100 micron.

* * * * *